United States Patent [19]
Von Behren et al.

[11] Patent Number: 5,619,999
[45] Date of Patent: Apr. 15, 1997

[54] BODY SURFACE POSITION LOCATOR FOR ULTRASOUND TRANSDUCER

[75] Inventors: Patrick L. Von Behren, Bellevue; David J. Thomas, Issaquah, both of Wash.

[73] Assignee: Siemens Medical Systems, Inc., Iselin, N.J.

[21] Appl. No.: 580,147

[22] Filed: Dec. 28, 1995

[51] Int. Cl.$^6$ .................................................. G03B 42/00
[52] U.S. Cl. ................................ 128/661.01; 73/862.046
[58] Field of Search .............................. 73/861.25, 602, 73/618; 128/661.07, 661.08, 661.09, 661.1, 662.01, 661.01

[56] References Cited

U.S. PATENT DOCUMENTS 5,172,343  12/1992  O'Donnell .

*Primary Examiner*—Richard Chilcot
*Assistant Examiner*—Ronald Biegel

[57] ABSTRACT

An ultrasound imaging system comprises a position location array adapted to be affixed to a surface layer of an imaging subject. The position location array comprises a plurality of electrodes disposed in a grid pattern within a flexible substrate. An imaging transducer having at least one element is operable to provide an acoustic pulse through the position location array and the surface layer in response to a driving signal and to provide a corresponding return signal in response thereto. A receiver is coupled to the imaging transducer to receive the return signal from the at least one element and provide a beamformed signal. A processor coupled to the receiver and the position location array forms an image from the beamformed signal that includes position coordinates that correspond to an intersection between the acoustic pulse and associated ones of the plurality of electrodes.

20 Claims, 3 Drawing Sheets

BODY SURFACE POSITION LOCATOR FOR ULTRASOUND TRANSDUCER

BACKGROUND OF THE INVENTION

1. Field of the Invention

This invention relates to ultrasonic diagnostic imaging, and more particularly, to an ultrasonic imaging system that precisely tracks the relative position of an ultrasound imaging transducer as it is traversed across a surface of an imaging subject.

2. Description of Related Art

Ultrasonic imaging techniques are commonly used to produce two-dimensional diagnostic images of internal features of an object, such as a human anatomy. A diagnostic ultrasonic imaging system for medical use forms images of internal tissues of a human body by electrically exciting an acoustic imaging transducer element or an array of acoustic transducer elements to generate short ultrasonic pulses that travel into the body. The ultrasonic pulses produce echoes as they reflect off of body tissues that appear as discontinuities or impedance changes to the propagating ultrasonic pulses. These echoes return to the imaging transducer, and are converted back into electrical signals that are amplified and decoded to produce a cross-sectional image of the tissues. These ultrasonic imaging systems are of significant importance to the medical field by providing physicians with real-time, high resolution images of the internal features of a human anatomy without resort to more invasive exploratory techniques, such as surgery.

The acoustic imaging transducer which radiates the ultrasonic pulses typically comprises a piezoelectric element or matrix of piezoelectric elements. As known in the art, a piezoelectric element deforms upon application of an electrical signal to produce the ultrasonic pulses. In a similar manner, the received echoes cause the piezoelectric element to deform and generate the corresponding electrical signal. The acoustic imaging transducer is often packaged within a portable or handheld device that allows a sonographer substantial freedom to easily manipulate the imaging transducer over a desired area of interest. The imaging transducer can then be electrically connected via a cable to a central control device that generates and processes the electrical signals. In turn, the control device transmits the image information to a real-time viewing device, such as a video display terminal. The image information may also be stored for later viewing of the diagnostic images.

The individual images produced by such ultrasonic imaging systems comprise discrete frames, with each such frame having a field of view defined by the region traversed by the ultrasonic pulses. As the imaging transducer is manipulated along the body surface to obtain tomographic image slices of an adjacent region in the anatomy, each previous image is replaced on the viewing device by a new image. A drawback of such systems is that the discrete frames do not include any coordinates that relate the precise transducer position to the physical region traversed by the imaging transducer. As a result, the sonographer cannot accurately return to a previously imaged position in order to monitor anatomical changes over time.

An image position location system would enable serial temporal monitoring of anatomical features, and would be of substantial benefit to surgical or therapeutic guidance. For example, such a system would provide accurate measurement of changes to size and position of a tumor, yielding critical information regarding the efficacy of a particular course of treatment. The position-located images could be compared to previously obtained ultrasound images, as well as to images obtained using other modalities such as computerized axial tomography (CAT), magnetic resonance imaging (MRI), or radiotherapy portal images. Moreover, the position-located images could be combined with other such images through known image fusion techniques. The compared or combined images could then provide a physician or sonographer with enhanced information concerning the transforming condition of body tissues which may otherwise be overlooked with serious potential consequences for the patient.

Previously, it has been demonstrated that imaging transducer position coordinates could be collected with a compound B-scanner utilizing a transducer mounted on an arm assembly. Either the arm assembly or the transducer element itself can be provided with sensing devices that track the precise position of the transducer. An example of a compound B-scanner utilizing angular sensing devices on an arm assembly is disclosed in U.S. Pat. No. 4,431,007, to Amazeen et al., for REFERENCED REAL-TIME ULTRASONIC IMAGE DISPLAY.

Despite this potential improvement in the art, conventional compound B-scanners are awkward and inflexible to operate due primarily to the relatively bulky mechanical arm assembly. An additional disadvantage of such scanners is that the correlation accuracy of images taken at different times depends upon the precise orientation of the patient relative to the arm assembly. Unless the patient is returned to the identical position with respect to a previous image scan, the position information obtained by the angular sensing devices would not correlate with the previously obtained position information.

Thus, a critical need exists for an ultrasound imaging apparatus that enables images to be position-located to the anatomical surface of the patient. The apparatus should be compatible with modern handheld ultrasonic imaging transducers without encumbering the transducers with position sensing devices that increase the cost, weight and complexity of such imaging systems.

SUMMARY OF THE INVENTION

In accordance with the teachings of this invention, an ultrasound imaging system is provided that enables images to be position-located to the anatomical surface of the patient.

The ultrasound imaging system comprises a position location array adapted to be affixed to a surface layer of an imaging subject. The position location array comprises a plurality of electrodes disposed in a grid pattern within a flexible substrate. An imaging transducer having at least one element is brought into contact with the position location array to provide an acoustic pulse that travels through the position location array and the patient's skin surface layer in response to a driving signal. The imaging transducer would also provide a corresponding return signal in response to the acoustic pulse. A receiver is coupled to the imaging transducer to receive the return signal from the transducer elements and provide a beamformed signal. A processor coupled to the receiver and the position location array forms an image from the beamformed signal that includes position coordinates that correspond to an intersection between the acoustic pulse and associated ones of the plurality of electrodes of the position location array.

More particularly, the flexible substrate is comprised of a piezoelectric material having an acoustic impedance substantially equivalent to an acoustic impedance of the surface layer of the patient so that the substrate does not appear in the ultrasound image. The flexible substrate may also comprise an adhesive layer disposed on a surface thereof to enable the substrate to be affixed to the surface layer of the patient. The grid pattern may be either a one or two-dimensional pattern.

The position location array may function with the processor in various alternative ways. In a first embodiment, the electrodes of the position location array detect the acoustic pulse emitted by the imaging transducer and convert the acoustic pulse to an electrical signal that is provided directly back to the processor. The processor determines position coordinates for the imaging transducer relative to the position location array based on the detected position signal.

In a second embodiment of the imaging system, the electrodes of the position location array respectively emit acoustic position signals in response to the acoustic pulse from the imaging transducer. The processor receives the position signals via the imaging transducer and differentiates the position signals from the beamformed signal to derive the location information.

In a third embodiment, the electrodes of the position location array constantly emit acoustic position signals independently of operation of the imaging transducer. As in the first embodiment, the imaging transducer detects the acoustic position signals and the processor differentiates the position signals from the beamformed signal to derive the location information.

DETAILED DESCRIPTION OF THE PREFERRED EMBODIMENT

Figure 1:
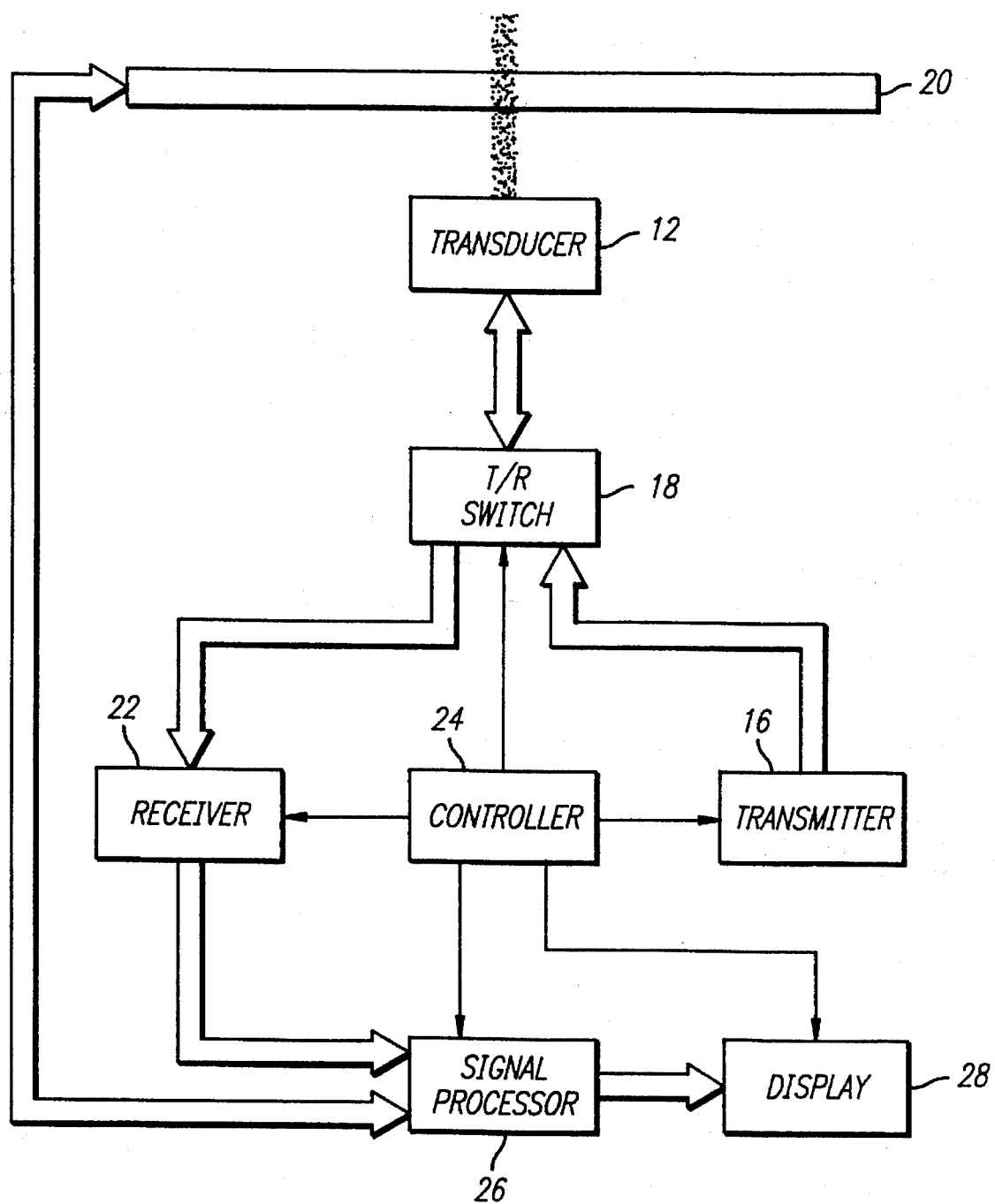
FIG. 1 is a block diagram of an ultrasonic imaging system having a position location transducer array.

This invention satisfies the critical need for an ultrasound imaging apparatus that enables images to be directly position-located to the anatomical surface of the patient. The apparatus is compatible with modern handheld ultrasonic imaging transducers without encumbering the transducers with position sensing devices that increase the cost, weight and complexity of such imaging systems. In the detailed description that follows, like reference numerals are used to describe like elements in one or more of the figures.

Referring first to FIG. 1, a block diagram of an ultrasonic imaging system is provided. The ultrasonic imaging system includes an imaging transducer array 12 comprised of a plurality of separately driven transducer elements. The imaging transducer array 12 may comprise either a one-dimensional array having a plurality of linearly disposed transducer elements, or a two-dimensional array in which the transducer elements are disposed in a matrix. In either configuration, the transducer elements produce acoustic pulses when energized by an electrical signal provided by a transmitter 16. The acoustic pulses travel through the various tissue layers of the patient, and are then reflected back from a region of interest to the imaging transducer 12 in the form of echo return pulses. The echo return pulses are converted by the imaging transducer 12 back into electrical signals that are routed to a receiver 22. A transmit/receive switch 18 controls the flow of signals from the transmitter 16 to the imaging transducer 12, and from the transducer to the receiver 22. The transmitter 16, receiver 22 and transmit/receive switch 18 are operated under the control of a central controller 24 that is responsive to commands by a sonographer that operates the ultrasonic imaging system.

A phased array sector scan is performed by controlling the phase of the signals applied by the transmitter 16 to each of the elements of the imaging transducer 12. By imparting a time delay to the electrical signal pulses provided to the successive transducer elements, the signal pulses cumulatively provide a net ultrasonic beam directed at an angle relative to a plane of the transducer array 12 toward a desired focal point. Progressive changes to the extent of the relative time delays causes the beam angle to change in an increment manner, thus steering the ultrasonic beam in a desired direction along a scan line. The echo return pulses from the focal point differ in phase and amplitude due to the differences in the propagation path travelled by the respective acoustic pulses.

The receiver 22 amplifies and demodulates the echo signals, imparts an appropriate time delay to each one of the echo signals, and sums the delayed echo signals together to provide a single beamformed signal that indicates the total ultrasonic energy reflected from the focal point. The receiver 22 typically includes an analog-to-digital converter that converts each of the analog echo signals into a series of digital values that can be sampled at a predetermined rate. The beamformed signal is then provided to the signal processor 26, where it is combined with like beamformed signals from other focal points of the scan lines to assemble a complete sector scan image. Finally, the signal processor 26 converts the plurality of beamformed signals into a data format that can be displayed as a graphical image on the video display terminal 28. The graphical image data may also be stored for later viewing, or printed to a hard-copy image.

To provide imaging transducer position-located information, the ultrasonic imaging system further comprises a position location transducer array 20. The position location array 20 is arranged relative to the imaging transducer 12 such that the acoustic pulses provided by the transducer element passes entirely through the array. As will be described in further detail below, the array 20 either passively, actively or reactively detects the acoustic pulses, and provides information regarding the physical coordinates of the acoustic pulses to the signal processor 26. The signal processor 26 assimilates the coordinate information from the array 20 into the data format representing each ultrasonic graphical image. As a result, the graphical images can be accurately position-located to the patient. The coordinate information may also be displayed on the video display terminal 28 along with the image.

Figure 2:
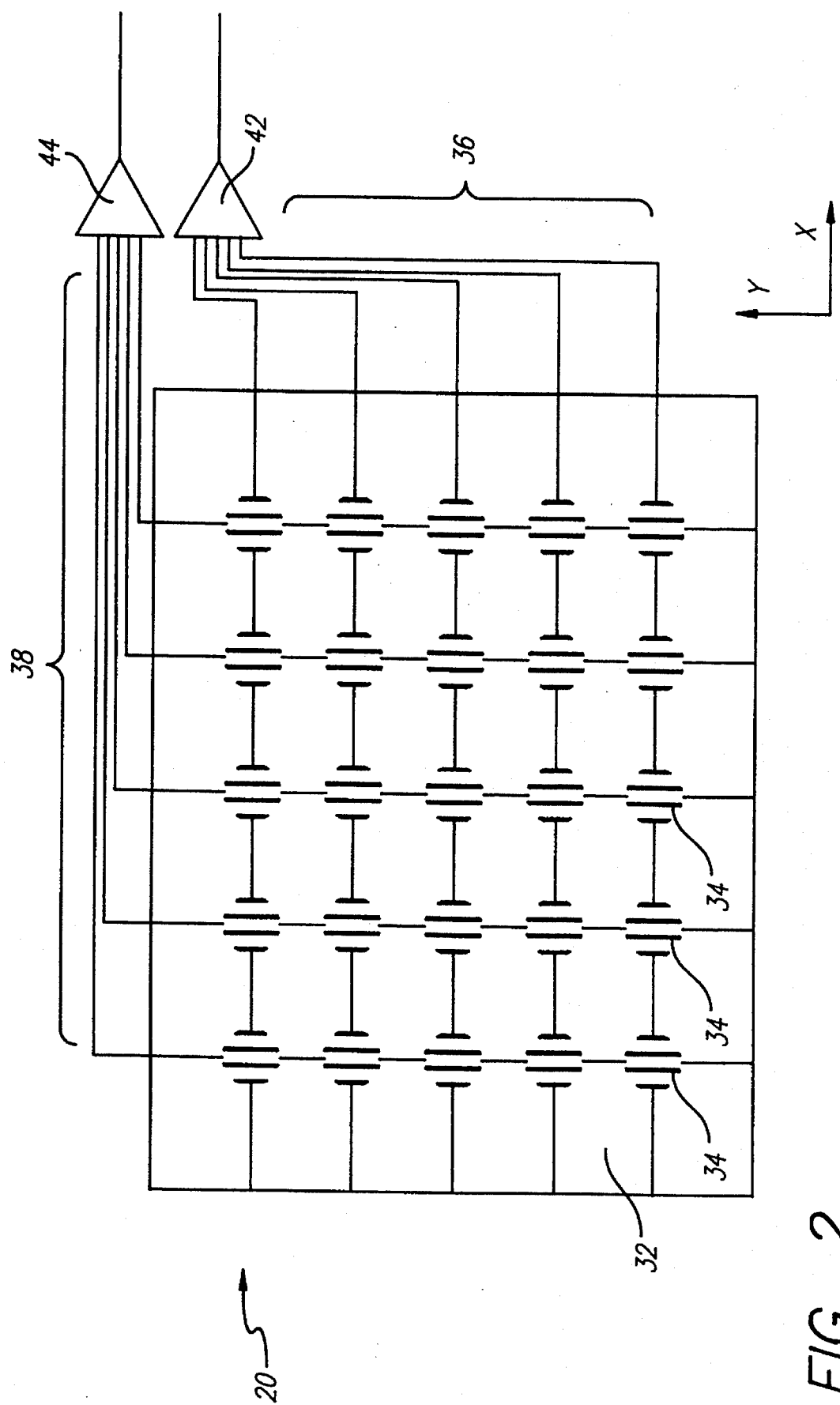
FIG. 2 is a front view of an enlarged portion of the position location transducer array.
Figure 3:
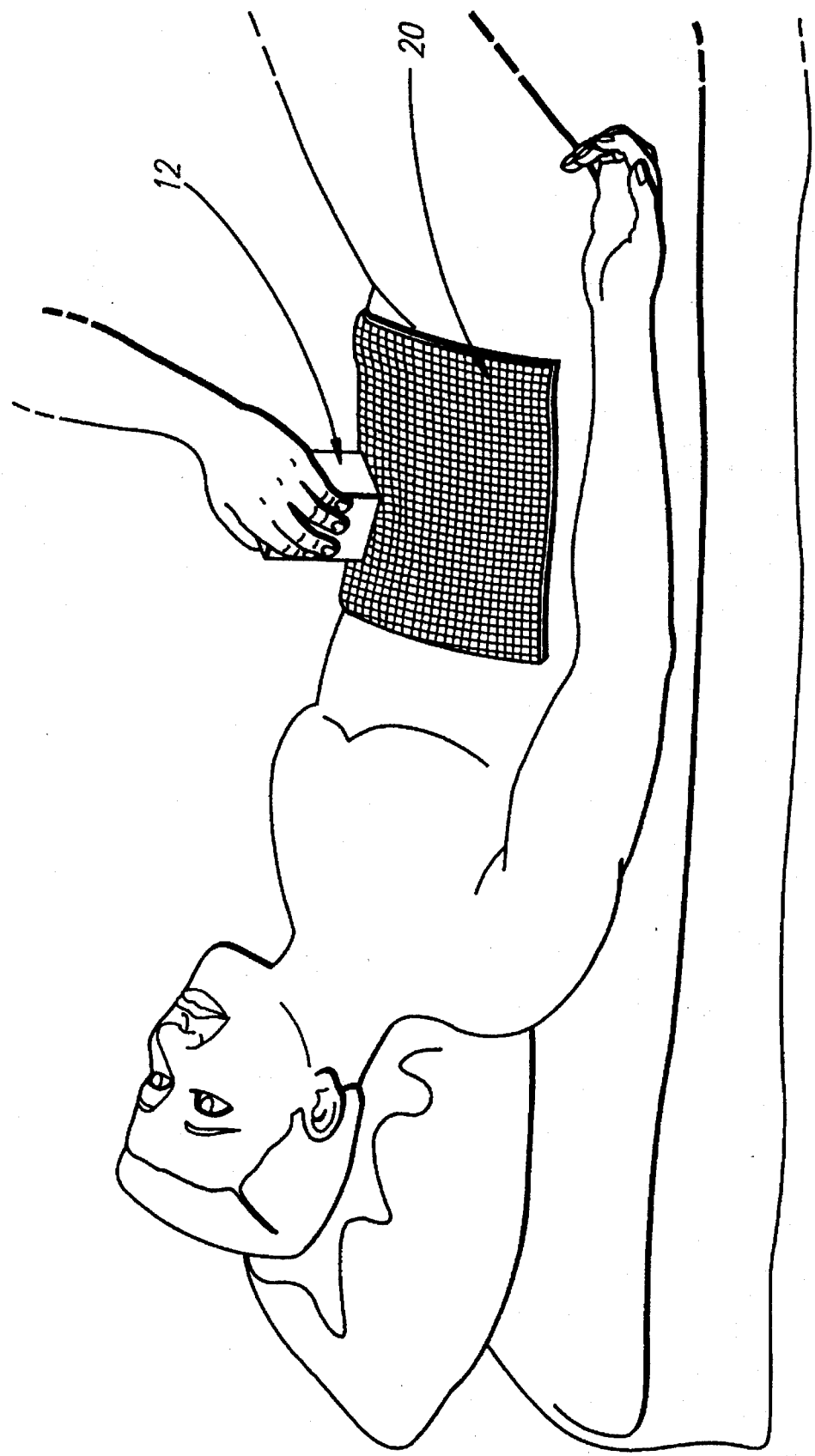
FIG. 3 illustrates the position location transducer array in use during an ultrasound imaging operation of an exemplary patient.

Referring now to FIGS. 2 and 3, the position location array 20 is illustrated in greater detail. The array 20 comprises a highly flexible and thin sheet of substrate 32 that would readily conform to the contours of a patient's skin surface, as shown in FIG. 3. The imaging transducer 12 would then be brought into direct contact with the substrate 32, and the acoustic pulses from the imaging transducer would travel through the substrate and into the patient's anatomy. The substrate 32 is formed from piezoelectric material, such as poly vinyl di-ethyl fluoride (PVDF), which has an acoustic impedance substantially equivalent to the acoustic impedance of the tissue layers of a patient. Thus, the substrate 32 would not appear in the ultrasound image.

As best illustrated in FIG. 2, a plurality of electrodes 34 are provided on the substrate 32 in a grid pattern. For purposes of illustration, a representative number of the electrodes 34 are identified in FIG. 2 within a first row of the grid pattern. The grid pattern may be two-dimensional having parallel rows and columns of electrodes 34, as shown in FIG. 2. Alternatively, the grid pattern may be one-dimensional having only a single row of electrodes 34. The spacing between the electrodes 34 and the number of electrodes may be arbitrarily selected based on the desired accuracy of the position-location information. For example, a greater number of closely spaced electrodes 34 would permit the array 20 to discern more fine distinctions in imaging transducer position; however, a higher number of electrodes would also require a greater amount of signal processing capability to process signal inputs from the electrodes. The electrodes 34 may be plated, printed or otherwise patterned onto the substrate 32 by conventional techniques.

The plurality of electrodes 34 are electrically coupled together in both the x and y-dimensions by electrical conductors 36, 38, respectively. The electrical conductors 36, 38 are then connected to amplifier devices 42, 44, respectively. As described below, the amplifier devices 42, 44 may either amplify signals received from the electrodes 34 in a passive or reactive mode, or alternatively, may amplify signals transmitted to the electrodes in an active mode. The amplifier devices 42, 44 may be integrally formed with the substrate 32, or may actually be located with and form part of the signal processor 26. Alternatively, the plurality of electrodes 34 may be individually connected to the signal processor 26.

In a first embodiment of the invention, the electrodes 34 operate in response to the acoustic pulses provided by the imaging transducer 12. The acoustic pulses cause the piezo-electric material of the substrate 32 to deform locally at the point of contact between the imaging transducer 12 and the substrate. This deformation of the substrate 32 causes an electrical signal to form on the electrodes 34 at or near the point of contract. The electrode 34 in closest proximity to the acoustic pulse would provide an electrical signal of highest relative amplitude. The amplifiers 42, 44 detect and amplify these signals from the electrodes 34, and transmit a multiplexed signal to the signal processor 26. The signal processor 26 can then localize which electrode or electrodes generated the highest amplitude signal from the multiplexed signal, and can accordingly determine the instantaneous position of the imaging transducer.

It should be apparent that the amplifiers 42, 44 may also operate in a digital manner by digitizing the electrical signals from the electrodes 34. The digitized signals could then be sampled at a particular sampling rate. By using a sampling rate substantially higher than an associated rate in which the imaging transducer 12 is moved, the signal processor 26 can thus determine the instantaneous location of the imaging transducer.

In a second embodiment, the electrodes 34 are triggered by the acoustic pulses from the imaging transducer 12 to generate an acoustic signal that is detected by the imaging transducer 12. The acoustic signal would then be differentiated from the beamformed signal from the receiver 22 by the signal processor 26. In this embodiment, the amplifiers 42, 44 operate in reverse from the previous embodiment and provide the electrodes 34 with an electrical signal. Each of the electrodes 34 may be provided with an electrical signal having a unique signature that characterizes the particular electrode. The signal processor 26 would then identify the location of the imaging transducer 12 from the unique signature.

In a third embodiment, the electrodes 34 provide an acoustic signal independently of the imaging transducer 12. The electrodes 34 would be constantly operating, and the imaging transducer 12 detects the acoustic signal from the electrodes. As in the previous embodiment, the acoustic signal would then be differentiated from the beamformed signal from the receiver 22 by the signal processor 26. The amplifiers 42, 44 may strobe the same electrical signal to drive the electrodes 34 in a sequential or raster pattern. The signal processor 26 would then identify the location of the imaging transducer 12 by time correlation based on the signal strobe rate.

It is anticipated that the substrate 32 may also have an adhesive layer disposed on a surface thereof to enable the substrate to be affixed to the skin surface of the patient. The substrate 32 may remain affixed to the patient's skin over a period of time, such as several days, during which a region may be repetitively imaged to provide a correlated image history. As known in the art, a sonographer may mark a patient's skin with an indelible marker so that the substrate 32 can be removed, and then re-affixed at a later date. To accommodate this, the substrate 32 may further be provided with indices or other markings to facilitate alignment with the skin markings. It is further anticipated that the substrate 32 be disposable to avoid the need for sterilization between serial uses of the array 20.

The invention is further defined by the following claims.

What is claimed is:

1. An imaging system, comprising:
   a position location array adapted to be affixed to a surface layer of an imaging subject, said position location array comprising a plurality of electrodes disposed in a grid pattern within a flexible substrate;
   a transducer having at least one element operable to provide an acoustic pulse through said position location array and said surface layer in response to a driving signal and to provide a corresponding return signal in response thereto;
   a receiver coupled to said transducer to receive said return signal from said at least one element and provide a beamformed signal; and
   processor means coupled to said receiver and said position location array for forming an image from said beamformed signal that includes position coordinates that correspond to an intersection between said acoustic pulse and associated ones of said plurality of electrodes.

2. The imaging system of claim 1, wherein said flexible substrate is comprised of a piezoelectric material having an acoustic impedance substantially equivalent to an acoustic impedance of said surface layer.

3. The imaging system of claim 1, wherein said flexible substrate further comprises an adhesive layer disposed on a surface thereof.

4. The imaging system of claim 1, wherein said grid pattern further comprises a one-dimensional pattern.

5. The imaging system of claim 1, wherein said grid pattern further comprises a two-dimensional pattern.

6. The imaging system of claim 1, further comprising a transmitter coupled to said transducer to provide said driving signal to said at least one element.

7. The imaging system of claim 1, wherein said associated ones of said plurality of electrodes emit a position signal in response to said acoustic pulse.

8. The imaging system of claim 7, wherein said processor means further comprises means for detecting said position signal from said plurality of electrodes.

9. The imaging system of claim 7, wherein said processor means further comprises means for detecting said position signal from said beamformed signal.

10. The imaging system of claim 1, wherein said processor means further comprises means for detecting said acoustic pulse from said plurality of electrodes.

11. In an ultrasonic imaging system having a transducer having at least one element operable to provide an acoustic pulse in response to a driving signal and to provide a corresponding return signal in response thereto, a position location system comprises:

a position location array adapted to be affixed to a surface layer of an imaging subject between said surface layer and said transducer, said position location array comprising a plurality of electrodes disposed in a grid pattern within a flexible substrate; and processor means coupled to said transducer and said position location array for forming an image from said return signal that includes position coordinates that correspond to an intersection between said acoustic pulse and associated ones of said plurality of electrodes.

12. The position location system of claim 11, wherein said flexible substrate is comprised of a material having an acoustic impedance substantially equivalent to an acoustic impedance of said surface layer.

13. The position location system of claim 11, wherein said flexible substrate is comprised of a piezoelectric material.

14. The position location system of claim 11, wherein said flexible substrate further comprises an adhesive layer disposed on a surface thereof.

15. The position location system of claim 11, wherein said grid pattern further comprises a one-dimensional pattern.

16. The position location system of claim 11, wherein said grid pattern further comprises a two-dimensional pattern.

17. The position location system of claim 11, wherein said associated ones of said plurality of electrodes emit a position signal in response to said acoustic pulse.

18. The position location system of claim 17, wherein said processor means further comprises means for detecting said position signal from said plurality of electrodes.

19. The position location system of claim 17, wherein said processor means further comprises means for detecting said position signal from said beamformed signal.

20. The position location system of claim 11, wherein said processor means further comprises means for detecting said acoustic pulse from said plurality of electrodes.

* * * * *